United States Patent
Manzi et al.

(10) Patent No.: US 8,246,630 B2
(45) Date of Patent: Aug. 21, 2012

(54) APPARATUS AND METHOD FOR INJECTING FLUENT MATERIAL AT A DISTRACTED TISSUE SITE

(75) Inventors: Richard Manzi, Yorktown Heights, NY (US); Tyler Lipschultz, New Canaan, CT (US); Peter Barreiro, West Haven, CT (US); Mark LoGuidice, Southport, CT (US); Thomas Wilson, Guilford, CT (US); Steve Wysocki, Stratford, CT (US)

(73) Assignee: Spine Wave, Inc., Shelton, CT (US)

( * ) Notice: Subject to any disclaimer, the term of this patent is extended or adjusted under 35 U.S.C. 154(b) by 248 days.

(21) Appl. No.: 12/858,530

(22) Filed: Aug. 18, 2010

(65) Prior Publication Data

US 2011/0004217 A1 Jan. 6, 2011

Related U.S. Application Data

(62) Division of application No. 11/031,562, filed on Jan. 7, 2005, now Pat. No. 7,789,912.

(60) Provisional application No. 60/535,407, filed on Jan. 8, 2004.

(51) Int. Cl.
*A61F 2/44* (2006.01)
(52) U.S. Cl. .............. 606/105; 606/93; 623/17.12
(58) Field of Classification Search .......... 606/90, 606/92–94, 105; 623/17.11–17.16
See application file for complete search history.

(56) References Cited

U.S. PATENT DOCUMENTS

| | | | |
|---|---|---|---|
| 3,750,667 A | 8/1973 | Pshenichny et al. | |
| 3,893,445 A | 7/1975 | Hofsess | |
| 4,142,517 A | 3/1979 | Stavropoulos et al. | |
| 4,313,434 A | 2/1982 | Segal | |
| 4,492,576 A | 1/1985 | Dragan | |
| 4,684,363 A | 8/1987 | Ari et al. | |
| 4,736,738 A | 4/1988 | Lipovsek et al. | |
| 4,793,351 A | 12/1988 | Landman et al. | |
| 4,904,260 A | 2/1990 | Ray et al. | |
| 4,969,888 A | 11/1990 | Scholten et al. | |

(Continued)

FOREIGN PATENT DOCUMENTS

EP 0277282 A1 10/1987

(Continued)

OTHER PUBLICATIONS

Premarket Notification [510(k)] Summary, Kyphx Directional Inflatable Bone Tamp-Traditional 510(k), Kyphon Inc., Jul. 16, 2003, (5 pgs).

(Continued)

*Primary Examiner* — Eduardo C Robert
*Assistant Examiner* — Tara Carter
(74) *Attorney, Agent, or Firm* — Hoffmann & Baron, LLP

(57) ABSTRACT

A system and method is provided for distracting opposite surfaces from the interior of a bone, such as a vertebral body. A working channel cannula provides a working channel through which an inserter and an injection cannula can simultaneously pass. The inserter transports a plurality of wafers into the interior of the bone to form a load-bearing stack bearing against the opposite surfaces. The injection cannula is used to inject a fluent material into and/or around the stack. In certain embodiments, the fluent material is a load-bearing or hardenable material, such as bone cement. In other embodiments, the fluent material can be a BMP, HAP, or other osteo-inductive, osteo-conductive, or pharmaceutical compositions. A syringe containing the fluent material is engaged to the injection cannula and is operable to inject the fluent material into the vertebral body under controlled pressure.

25 Claims, 5 Drawing Sheets

U.S. PATENT DOCUMENTS

| | | | |
|---|---|---|---|
| 5,108,404 A | 4/1992 | Scholten et al. |
| 5,219,328 A | 6/1993 | Morse et al. |
| 5,300,035 A | 4/1994 | Clement |
| 5,318,524 A | 6/1994 | Morse et al. |
| 5,331,975 A | 7/1994 | Bonutti |
| 5,411,491 A | 5/1995 | Goldhardt et al. |
| 5,431,676 A | 7/1995 | Dubrul et al. |
| 5,443,514 A | 8/1995 | Steffee |
| 5,468,245 A | 11/1995 | Vargas, III |
| 5,505,732 A | 4/1996 | Michelson |
| 5,514,153 A | 5/1996 | Bonutti |
| 5,549,565 A | 8/1996 | Ryan et al. |
| 5,556,429 A | 9/1996 | Felt |
| 5,562,736 A | 10/1996 | Ray et al. |
| 5,645,597 A | 7/1997 | Krapiva |
| 5,667,520 A | 9/1997 | Bonutti |
| 5,681,289 A | 10/1997 | Wilcox et al. |
| 5,685,826 A | 11/1997 | Bonutti |
| 5,697,889 A | 12/1997 | Slotman et al. |
| 5,702,446 A | 12/1997 | Schenck et al. |
| 5,716,416 A | 2/1998 | Lin |
| 5,720,726 A | 2/1998 | Marcadis et al. |
| 5,752,969 A | 5/1998 | Cunci et al. |
| 5,762,629 A | 6/1998 | Kambin |
| 5,800,549 A | 9/1998 | Bao et al. |
| 5,819,497 A | 10/1998 | Knepper |
| 5,827,318 A | 10/1998 | Bonutti |
| 5,860,997 A | 1/1999 | Bonutti |
| 5,888,220 A | 3/1999 | Felt et al. |
| 5,954,739 A | 9/1999 | Bonutti |
| 6,017,305 A | 1/2000 | Bonutti |
| 6,017,350 A | 1/2000 | Long |
| 6,030,401 A | 2/2000 | Marino |
| 6,039,761 A | 3/2000 | Li et al. |
| 6,042,596 A | 3/2000 | Bonutti |
| 6,048,346 A | 4/2000 | Reiley et al. |
| 6,063,378 A | 5/2000 | Nohara et al. |
| 6,083,202 A | 7/2000 | Smith |
| 6,113,639 A | 9/2000 | Ray et al. |
| 6,123,687 A | 9/2000 | Simonyi et al. |
| 6,126,682 A | 10/2000 | Sharkey et al. |
| 6,135,999 A | 10/2000 | Fanton et al. |
| 6,140,452 A | 10/2000 | Felt et al. |
| 6,174,311 B1 | 1/2001 | Branch et al. |
| 6,183,518 B1 | 2/2001 | Ross et al. |
| 6,187,023 B1 | 2/2001 | Bonutti |
| 6,187,048 B1 | 2/2001 | Milner et al. |
| 6,206,921 B1 | 3/2001 | Guagliano et al. |
| 6,210,376 B1 | 4/2001 | Grayson |
| 6,210,397 B1 | 4/2001 | Aboul-Hosn et al. |
| 6,224,599 B1 | 5/2001 | Baynham et al. |
| 6,224,630 B1 | 5/2001 | Bao et al. |
| 6,245,107 B1 | 6/2001 | Ferree |
| 6,248,110 B1 | 6/2001 | Reiley et al. |
| 6,248,131 B1 | 6/2001 | Felt et al. |
| 6,261,311 B1 | 7/2001 | Sharkey et al. |
| 6,264,659 B1 | 7/2001 | Ross et al. |
| 6,277,122 B1 | 8/2001 | McGahan et al. |
| 6,306,177 B1 | 10/2001 | Felt et al. |
| 6,312,469 B1 | 11/2001 | Gielen et al. |
| 6,312,725 B1 | 11/2001 | Wallace et al. |
| 6,332,894 B1 | 12/2001 | Stalcup et al. |
| 6,340,369 B1 | 1/2002 | Ferree |
| 6,344,058 B1 | 2/2002 | Ferree |
| 6,370,420 B1 | 4/2002 | Kraft |
| 6,371,990 B1 | 4/2002 | Ferree |
| 6,395,007 B1 | 5/2002 | Bhatnagar et al. |
| 6,402,750 B1 | 6/2002 | Atkinson et al. |
| 6,402,784 B1 | 6/2002 | Wardlaw |
| 6,423,333 B1 | 7/2002 | Stedronsky et al. |
| 6,425,919 B1 | 7/2002 | Lambrecht |
| 6,428,576 B1 | 8/2002 | Haldimann |
| 6,436,143 B1 | 8/2002 | Ross et al. |
| 6,440,138 B1 | 8/2002 | Reiley et al. |
| 6,443,988 B2 | 9/2002 | Felt et al. |
| 6,447,512 B1 | 9/2002 | Landry et al. |
| 6,482,235 B1 | 11/2002 | Lambrecht et al. |
| 6,500,205 B1 | 12/2002 | Michelson |
| 6,508,839 B1 | 1/2003 | Lambrecht et al. |
| 6,558,390 B2 | 5/2003 | Cragg |
| 6,579,291 B1 | 6/2003 | Keith et al. |
| 6,592,625 B2 | 7/2003 | Cauthen |
| 6,595,998 B2 | 7/2003 | Johnson et al. |
| 6,726,691 B2 | 4/2004 | Osorio et al. |
| 6,740,093 B2 | 5/2004 | Hochschuler et al. |
| 6,805,695 B2 | 10/2004 | Keith et al. |
| 6,814,736 B2 | 11/2004 | Reiley et al. |
| 6,981,981 B2 | 1/2006 | Reiley et al. |
| 7,004,945 B2 | 2/2006 | Boyd et al. |
| 7,112,205 B2 | 9/2006 | Carrison |
| 7,261,720 B2 | 8/2007 | Stevens et al. |
| 7,294,132 B2 | 11/2007 | Raskin et al. |
| 7,338,493 B1 | 3/2008 | Vandewalle |
| 2001/0021852 A1 | 9/2001 | Chappius |
| 2002/0032155 A1 | 3/2002 | Ferree |
| 2002/0045942 A1 | 4/2002 | Ham |
| 2002/0049498 A1 | 4/2002 | Yuksel et al. |
| 2002/0049527 A1 | 4/2002 | Kohno et al. |
| 2002/0099385 A1 | 7/2002 | Ralph et al. |
| 2002/0111688 A1 | 8/2002 | Cauthen |
| 2002/0120337 A1 | 8/2002 | Cauthen |
| 2002/0123807 A1 | 9/2002 | Cauthen, III |
| 2002/0147497 A1 | 10/2002 | Belef et al. |
| 2002/0151980 A1 | 10/2002 | Cauthen |
| 2002/0156531 A1 | 10/2002 | Felt et al. |
| 2002/0183761 A1 | 12/2002 | Johnson et al. |
| 2002/0189622 A1 | 12/2002 | Cauthen, III et al. |
| 2003/0009227 A1 | 1/2003 | Lambrecht et al. |
| 2003/0033017 A1 | 2/2003 | Lotz et al. |
| 2003/0082169 A1 | 5/2003 | Boyd |
| 2003/0083642 A1 | 5/2003 | Boyd et al. |
| 2003/0120345 A1 | 6/2003 | Cauthen |
| 2004/0059339 A1 | 3/2004 | Roehm, III et al. |
| 2004/0068268 A1 | 4/2004 | Boyd et al. |
| 2004/0073213 A1 | 4/2004 | Serhan et al. |
| 2004/0098017 A1 | 5/2004 | Saab et al. |
| 2004/0186471 A1 | 9/2004 | Trieu |
| 2004/0229878 A1 | 11/2004 | DiMauro et al. |
| 2005/0070913 A1 | 3/2005 | Milbocker et al. |
| 2005/0102030 A1 | 5/2005 | Yuksel et al. |
| 2005/0209602 A1 | 9/2005 | Bowman et al. |
| 2005/0234425 A1 | 10/2005 | Miller et al. |

FOREIGN PATENT DOCUMENTS

| | | |
|---|---|---|
| FR | 2639823 | 8/1990 |
| WO | 91/00713 A1 | 1/1991 |
| WO | 01/68005 A2 | 9/2001 |

OTHER PUBLICATIONS

510(k) Summary of Safety and Effectiveness, "KyphX™ Inflatable Bone Tamp", Jan. 25, 2001 (5 pgs).

Boyd, Lawrence M., Mahar, Andrew and Cappello, Joseph, "Injectable Biomaterials for Augmentation of the Nucleus Pulposus", International Symposium—Non Fusion Techniques in Spinal Surgery, Feb. 14-15, 2003, (12 pgs).

Mahar, Andrew, Oka, Richard, Whitledge, Jon, Cappello, Joseph R., Powell, Jim, McArthur, Tina, Capello, Joseph, "Biomechanical Efficacy of a Protein Polymer Hydrogel for Inter-Vertebral Nucleus Augmentation and Replacement", World Congress on Biomechanics, Calgary, Canada, Aug. 5, 2002, (4 pgs).

Kitchel, Scott and Cappello, Joseph, "Injectable Biomaterials for Augmentation of the Nucleus Pulposus", http://127.0.0.1:8080/SAS3C1/presentation_list8.php, Apr. 26, 2005, (6 pgs).

Garfin, Steven R., Yuan, Hansen A. and Reiley, Mark A., "Kyphoplasty and Vertebroplasty for the Treatment of Painful Osteoporotic Compression Fractures", SPINE, vol. 26, No. 14, 2001, pp. 1511-1515.

Lieberman, I.H., Dudeney, S., Reinhardt, M.K. and Bell, G., "Initial Outcome and Efficacy of "Kyphoplasty" in the Treatment of Painful Osteoporotic Vertebral Compression Fractures", SPINE, vol. 26, No. 14, pp. 1631-1638, 2001, (8 pgs).

APPARATUS AND METHOD FOR INJECTING FLUENT MATERIAL AT A DISTRACTED TISSUE SITE

REFERENCE TO RELATED APPLICATION

This application claims priority to, and is a division of, application Ser. No. 11/031,562, filed on Jan. 7, 2005, now U.S. Pat. No. 7,789,912, the disclosure of which is incorporated herein by reference, which claims priority to provisional application No. 60/535,407, filed on Jan. 8, 2004, the disclosure of which is incorporated herein by reference.

BACKGROUND OF THE INVENTION

The present invention involves the field of surgery, and particularly orthopaedic surgery. The invention relates to surgical instruments and procedures involved in the distraction of adjacent tissue surfaces.

A variety of physical conditions involve two tissue surfaces that, for treatment of the condition, need to be distracted from one another and then supported away from one another. Such distraction may be to gain exposure to select tissue structures, to apply a therapeutic pressure to select tissues, to return tissue structures to their anatomic position and form, or in some cases to deliver a drug or growth factor to alter, influence or deter further growth of select tissues. Depending on the condition being treated, the tissue surfaces may be opposed or contiguous and may be bone, skin, soft tissue, or a combination thereof. An optimal treatment method includes distracting and supporting the tissue surfaces simultaneously.

A minimally invasive distraction and support device has significant application in orthopaedic surgical procedures, including acute and elective procedures to treat bone fractures and degenerative changes of the skeletal system and including vertebral compression fractures, interbody fusion, vertebral disc augmentation or replacement, and other compression fractures including, but not limited to tibial plateau compression fractures, calcaneous compression fractures, distal tibia fractures, distal radius (wrist) fractures, crushed or fractured orbit and orthopaedic oncology. Further, a minimally invasive distraction and support device has application in non-orthopaedic surgical procedures in plastic surgery (for example facial reconstruction), gastrointestinal surgery and urological surgery (for example the treatment of incontinence).

Vertebral Compression Fractures

A vertebral compression fracture is a crushing injury to one or more vertebrae. Vertebral fractures are generally associated with osteoporosis (the "brittle bone" disease), metastasis, and/or trauma. Osteoporosis reduces bone density, thereby weakening bones and predisposing them to fracture.

The osteoporosis-weakened bones can collapse during normal activity. In severe cases of osteoporosis, actions as simple as bending forward can be enough to cause a vertebral compression fracture. Vertebral compression fractures are the most common type of osteoporotic fractures according to the National Institute of Health. The mechanism of these fractures is one of flexion with axial compression where even minor events cause damage to the weak bone. While the fractures may heal without intervention, the crushed bone may fail to heal adequately. Moreover, if the bones are allowed to heal on their own, the spine will be deformed to the extent the vertebrae were compressed by the fracture. Spinal deformity may lead to breathing and gastrointestinal complications, and adverse loading of adjacent vertebrae.

Vertebral fractures happen most frequently at the thoracolumbar junction, with a relatively normal distribution of fractures around this point. Vertebral fractures can permanently alter the shape and strength of the spine. Commonly, they cause loss of height and a humped back. This disorder (called kyphosis or "dowager's hump") is an exaggeration of the spinal curve that causes the shoulders to slump forward and the top of the back to look enlarged and humped. In severe cases, the body's center of mass is moved further away from the spine resulting in increased bending moment on the spine and increased loading of individual vertebrae.

Another contributing factor to vertebral fractures is metastatic disease. When cancer cells spread to the spine, the cancer may cause destruction of part of the vertebra, weakening and predisposing the bone to fracture. Osteoporosis and metastatic disease are common root causes leading to vertebral fractures, but trauma to healthy vertebrae also causes minor to severe fractures. Such trauma may result from a fall, a forceful jump, a car accident, or any event that stresses the spine past its breaking point. The resulting fractures typically are compression fractures or burst fractures.

Vertebral fractures can occur without pain. However, they often cause a severe "band-like" pain that radiates from the spine around both sides of the body. It is commonly believed that the source of acute pain in compression fractures is the result of instability at the fracture site, allowing motion that irritates nerves in and around the vertebrae.

Until recently, treatment of vertebral compression fractures has consisted of conservative measures including rest, analgesics, dietary, and medical regimens to restore bone density or prevent further bone loss, avoidance of injury, and bracing. Unfortunately, the typical patient is an elderly person who generally does not tolerate extended bed rest well. As a result, minimally invasive surgical methods for treating vertebral compression fractures have recently been introduced and are gaining popularity.

One technique used to treat vertebral compression fractures is injection of bone filler into the fractured vertebral body. This procedure is commonly referred to as percutaneous vertebroplasty. Vertebroplasty involves injecting bone filler (for example, bone cement) into the collapsed vertebra to stabilize and strengthen the crushed bone.

In vertebroplasty, physicians typically use one of two surgical approaches to access thoracic and lumbar vertebral bodies: transpedicular or extrapedicular. The transpedicular approach involves the placement of a needle or wire through the pedicle into the vertebral body, and the physician may choose to use either a unilateral access or bilateral transpedicular approach. The second approach, the extrapedicular technique, involves an entry point through the posterolateral corner of the vertebral body. The needle entry point is typically 8 cm to 12 cm lateral of the mid-sagittal plane, with the skin incision typically closer to 8 cm in the proximal spine and generally closer to 12 cm in the distal spine. In general, one cannula is placed to fill the vertebral body with the extrapedicular approach.

Regardless of the surgical approach, the physician generally places a small diameter guide wire or needle along the path intended for the bone filler delivery needle. The guide wire is advanced into the vertebral body under fluoroscopic guidance to the delivery point within the vertebrae. The access channel into the vertebra may be enlarged to accommodate the delivery tube. In some cases, the delivery tube is placed directly and forms its own opening. In other cases, an access cannula is placed over the guide wire and advanced into the vertebral body. After placement, the cannula is replaced with the delivery tube, which is passed over the guide pin. In both cases, a hollow needle or similar tube is placed into the vertebral body and used to deliver the bone filler into the vertebra.

In this procedure, lower viscosities and higher pressures tend to disperse the bone filler throughout the vertebral body. However, such conditions dramatically increase the risk of bone filler extravasation from the vertebral body. The transpedicular approach requires use of a relatively small needle (generally 11 gauge or smaller). In contrast, the extrapedicular approach provides sufficient room to accommodate a larger needle (up to 6 mm internal diameter in the lumbar region and lower thoracic regions). In general, the small diameter needle required for a transpedicular approach necessitates injecting the bone filler in a more liquid (less viscous) state. Further, the pressure required to flow bone filler through a small gauge needle is relatively high. The difficulty of controlling or stopping bone filler flow into injury sensitive areas increases as the required pressure increases. The larger needle used in the extrapedicular approach allows injection of bone filler in a thicker, more controllable viscous state. Therefore, many physicians now advocate the extrapedicular approach so that the bone filler may be delivered through a larger cannula under lower pressure.

Caution must be taken to prevent extravasation, with the greatest attention given to preventing posterior extravasation because it may cause spinal cord trauma. Physicians typically use fluoroscopic imaging to monitor bone filler propagation and to avoid flow into areas of critical concern. If a foraminal leak results, the patient may require surgical decompression and/or suffer paralysis.

Kyphoplasty is a modified vertebral fracture treatment that uses one or two balloons, similar to angioplasty balloons, to attempt to reduce the fracture and restore vertebral height prior to injecting the bone filler. Two balloons are typically introduced into the vertebra via bilateral transpedicular cannulae. The balloons are inflated to reduce the fracture. After the balloon(s) is deflated and removed, leaving a relatively empty cancellous bone, bone cement is injected into the vertebra. In theory, inflation of the balloons restores vertebral height. However, it is difficult to consistently attain meaningful height restoration. It appears the inconsistent results are due, in part, to the manner in which the balloon expands in a compressible media and the structural orientation of the trabecular bone within the vertebra.

Tibial Plateau Compression Fractures

A tibial plateau fracture is a crushing injury to one or both of the tibial condyles resulting in a depression in the articular surface of the condyle. In conjunction with the compression fracture, there may be a splitting fracture of the tibial plateau. Appropriate treatment for compression fractures depends on the severity of the fracture. Minimally displaced compression fractures may be stabilized in a cast or brace without surgical intervention. More severely displaced compression with or without displacement fractures are treated via open reduction and internal fixation.

Typically, the underside of the compression fracture is accessed either through a window cut (a relatively small resection) into the side of the tibia or by opening or displacing a splitting fracture. A bone elevator is then used to reduce the fracture and align the articular surface of the tibial condyle. Bone filler is placed into the cancellous bone under the reduced compression fracture to maintain the reduction. If a window was cut into the side of the tibia, the window is packed with graft material and may be secured with a bone plate. If a splitting fracture was opened to gain access, then the fracture is reduced and may be stabilized with bone screws, bone plate and screws, or a buttress plate and screws.

Spinal Interbody Fusion

Spinal fusion is most frequently indicated to treat chronic back pain associated with instability or degenerative disc disease that has not responded to less invasive treatments. Fusion is also prescribed to treat trauma and congenital deformities. Spinal fusion involves removal of the spinal disc and fusing or joining the two adjacent vertebrae. The primary objective for patients suffering from instability is to diminish the patient's pain by reducing spinal motion.

Spinal fusions are generally categorized into two large groups: instrumented and non-instrumented. In non-instrumented procedures, the physician removes tissue from the unstable disc space and fills it with some form of bone graft that facilitates the fusion of the two adjacent vertebral bodies. Instrumented procedures are similar to non-instrumented procedures, except that implants (generally metallic) are also applied to further stabilize the vertebrae and improve the likelihood of fusion.

Conventional instrumented procedures generally utilize plates, rods, hooks, and/or pedicle screws through various surgical approaches. These conventional implants are secured to the vertebral bodies that are being fused. Interbody fusion devices were introduced in the 1990's as a less invasive surgical alternative, although interbody devices are increasingly being used in conjunction with pedicle screws. Interbody devices are implanted into the disc space to restore the normal disc spacing, utilizing tension in the annulus to stabilize the fusion unit. Interbody fusion provides a large area of the vertebral end plate for establishing bony fusion, a viable blood supply from the decorticated end plates, and dynamic compressive loading of the graft site. The interbody devices are generally filled with a bone filler to facilitate fusion. Interbody devices can be categorized in three primary groups: spinal fusion cages, which are available in a variety of shapes including rectangular, round-faced, and lordotic; allograft bone dowels and wedges (which are also available in various shapes); and titanium mesh (although titanium mesh is not itself a structural spacer).

Interbody fusion is typically completed through a posterior, an anterior, or a lateral inter-transverse approach. Each of these techniques has limitations. Lumbar interbody fusion presents a challenging surgical procedure and relatively high pseudoarthrosis rates. As a result, this approach is increasingly combined with additional internal fixation devices such as pedicle screw fixation.

In all interbody surgical approaches, a relatively large opening is made in the annulus. The nuclear material is removed and the end plates are decorticated to facilitate bony fusion. Overall, the use of interbody devices has resulted in mixed clinical outcomes. Placement of a fixed height device presents challenges in proper tensioning of the annulus. For these and other reasons, there is concern over long-term stability of interbody devices and fusion mass.

Distraction Systems and Methods

One approach to address the concerns in the various surgical procedures discussed above is presented in U.S. Pat. No. 6,595,998, which issued on Jul. 22, 2003, and which is owned by the assignee of the present invention. The disclosure of the '998 Patent is expressly incorporated herein by reference. The system in the '998 Patent provides a combination of a temporary or long term implantable device and instrumentation to place the device, in which tissue surfaces are distracted along an axis to enable access to the space between the tissues. Generally, the '998 Patent discloses solid wafers for stacking upon one another to provide an axially extending column to distract and support tissue surfaces. While a primary use of that invention is to reduce and stabilize vertebral compression fractures, the disclosed devices and methods may be used in any situation where it is desirable to distract two tissue surfaces. The tissues may be bone, skin, soft tissue, or combinations thereof. Further, the surfaces may be opposed surfaces of contiguous elements or surfaces of opposed elements. The '998 Patent discloses devices and methods that may be used to treat vertebral compression fractures, for replacement of vertebral discs, as an interbody fusion device, wedge opening high tibial osteotomy, tibial tuberosity elevation, as well as for treating other compression fractures including, but not limited to tibia plateau fractures, calcaneous, distal tibial fractures, or distal radius (wrist) fractures.

The '998 Patent concerns a distraction device or solid scaffold or support structure that includes a plurality of stackable wafers designed for insertion between tissue surfaces to form a column. The wafer column is assembled percutaneously in vivo to provide a distraction force as well as support and stabilization of the distracted tissue. Preferably, the wafers place distraction force in one direction only and thus provide directional distraction. The distraction device may be permanently implanted, in which case the wafer column may be used alone or in conjunction with a bone filler material. Alternately, the distraction device may be used temporarily to manipulate tissues and then removed.

In use, the wafers are preferably stacked between two tissue surfaces as they are implanted, thereby distracting and supporting the tissue surfaces simultaneously. Use of the devices and methods of the '998 Patent to treat a vertebral compression fracture is depicted in FIG. 1. A series of wafers 11 are transported through a working channel cannula 15 into the cancellous bone C of a vertebral body $V_1$. The wafers 11 are continually inserted into the cancellous bone, distracting the superior and inferior bony surfaces of the vertebral body $V_1$ as the stack 10 of wafers grows. The wafers may be used to distract other tissue surfaces, such as between the tibial plateau and associated condyle.

In one embodiment, the wafers are designed to be beveled at both their leading and trailing edges so that when lined up end-to-end, force on the trailing edge of the trailing wafer causes its leading edge to slide below the trailing edge of the leading wafer, thereby lifting up the leading wafer. Likewise, the bevel of the leading and trailing edges may be reversed enabling insertion of a trailing wafer above a leading wafer. Alternately, the leading and trailing edges may be chevron shaped or curved when viewed from the side, enabling insertion of trailing wafers between any two leading wafers or on the top or bottom of the column. In another embodiment, the wafers may be configured with blunt edges wherein the wafers are stacked with the insertion instrument. In all embodiments, by repeating the process with consecutive wafers, the column height increases to restore vertebral height.

In order to place the wafers between the tissue surfaces, the '998 Patent discloses a wafer inserter 12, as depicted in FIG. 2, that includes the track 13 positioned within the surgical site with access at its distal tip to the tissue surfaces to be distracted and supported. Wafers can be fed from a cartridge 14. As disclosed in the '998 Patent, the inserter includes a plunger is that is used to advance the wafer to the distal end of the cannula. This is repeated with consecutive wafers until a column of sufficient height is created per physician discretion. After the wafer(s) have been inserted, the insertion device is removed. The distal end of the insertion device may be manufactured from the same material as the wafers and/or be detachable. In this embodiment, the distal end of the insertion instrument would be detached after placing the wafer column, and the instrument removed.

The wafers disclosed in the '998 Patent may be formed from a solid form of bone filler material, and/or any other suitable material such as but not limited to implantable grade alloys (including, but not limited to titanium, cobalt chrome, nitinol, or stainless steel), other medical grade composites (including, but not limited to polyetheretherketone polymer (PEEK), ultra-high molecular weight polyethylene, or polyethylene) other ceramics (including, but not limited to zirconia, alumina, or calcium-phosphate based ceramics), and resorbable polymers (for example, polylactic acid (PLA), polyglycolic acid (PGA), and poly(lactide-coglycolide) (PLGA)). The wafers may be dense or porous, while porous wafers may be filled with resorbable polymers to increase mechanical strength. For soft tissue applications, it may be desirable to manufacture the wafers of woven collagen pads, tissue engineered materials, chitin, urethanes, silicone, or silicone materials. Alternately, the wafers may be manufactured from hydrogel (polyvinyl alcohol) in which the wafer is inserted in a dehydrated form and expands with fluids present at the insertion site. Hydrogel wafers may be particularly desirable for placing in the disc space between vertebrae. For purposes of this disclosure, these materials and their combinations will be collectively defined as the "implant materials."

Further, the wafers and implant materials may be combined with osteoinductive agents (including BMPs, growth factors, cell therapy, gene therapy, and patient derived factors) and other drug therapies. The osteoinductive agents may be added to initiate and accelerate bone formation while the drug therapies may range from antibiotics to reduce the risk of infection to chemotherapy to treat cancer. Optionally, the wafers may be used with a flowable bone filler material, which may be defined as any substance used to stabilize the bone. Suitable bone filler material includes, but is not limited to, bone cement (polymethyl methacrylate PMMA, or PMA), other composite material, human bone graft (allograft or autograft), synthetic and xenograft derived bone substitutes (calcium phosphate, hydroxylapatite, and/or other ceramic based bone substitutes), collagen, or combinations of these materials.

It is disclosed in the '998 Patent that in certain applications, it may be beneficial for the wafers to be secured to one another after insertion. Any suitable method for securing the wafers to one another as known by those skilled in the arts may be used. Wafers may be secured to one another by means of an adhesive bond, a chemical bond, and/or a mechanical interlock (as described above). Applying a generic fluent adhesive, for example cyanoacrylate, around the column provides adhesive bonding. The fluent adhesive hardens and locks the wafers.

Introducing a liquid material that is chemically equivalent to the wafer provides a potential chemical bonding. For example, the wafers may be manufactured from bone cement and bone cement may be injected around the wafers and into the vertebral body. The monomer in the bone cement may initiate a chemical bonding between the wafer and the bone filler, thereby locking the wafers together. A stable construct combined with cement interdigitation is believed to provide stability and pain relief in a crushed vertebra.

The devices and methods of the '998 Patent address various inabilities in the prior art to adequately distract opposing tissue surfaces. The devices disclosed in the '998 Patent are particularly beneficial in restoring the vertebral body to its intended anatomic height following a compression fracture. However, even with this improvement, there still remains a need for devices and methods for introducing fluent or liquid material into the distraction site, and particularly adjacent to or around the height restoring or load bearing distraction component. The fluent material may itself provide structural or load bearing capabilities, or may be non-structural but still capable of alleviating pain associated with the fracture.

SUMMARY OF THE INVENTION

In order to address this need, the present invention contemplates a method for distracting surfaces of a bone comprising the steps of: introducing a solid distraction component within the interior of the bone between opposite surfaces of the bone to maintain the surfaces in a distracted position; introducing an injection cannula directly into the cancellous portion of the bone adjacent the distraction component; and injecting a fluent material through the injection cannula directly into the interior of the bone adjacent the distraction component.

In accordance with this method, the fluent material is injected directly within the cancellous portion of the bone, rather than indirectly at an opening in the cortical bone. Moreover, the fluent material is injected so that it can at least partially surround the distraction component and, in the preferred embodiment, interdigitate with the surrounding cancellous bone.

Preferably, the injecting step includes injecting the fluent material under pressure. However, the pressure is less than a pressure at which extravasion occurs from the bone.

In certain embodiments, the fluent material is a hardenable material, such as a bone cement. In other embodiments, the fluent material is a non-structural fluid, while in other cases, the fluent material is selected from the group containing hydroxyapatite, bone morphogenic protein, osteo-inductive compositions, osteo-conductive compositions and pharmaceutical compositions.

In one aspect of the invention, the method further comprises the step of providing access to the interior of the bone through a working channel cannula. With the addition of this step, the steps of introducing the distraction component and the injection cannula occur through this same working channel cannula. The working channel cannula may be imbedded within an access portal in the cortical portion of the bone, or slightly retracted from the access portal in the cortical bone.

In accordance with one aspect of the invention, the injection cannula includes a plurality of openings, and the injecting step includes positioning the injection cannula so that the plurality of openings are oriented so that fluent material is injected therethrough directly adjacent the distraction component. In another aspect, the injection cannula includes a single angled opening at the distal tip of the cannula, and the injecting step includes positioning the injection cannula so that the angled opening is oriented so that fluent material is injected therethrough directly adjacent the distraction component.

In the preferred embodiment, the injecting step includes engaging a syringe containing the fluent material to the injection cannula, and depressing the plunger of the syringe to inject the fluent material through the injection cannula. Multiple syringes may be provided where different or additional fluent material is required.

In accordance with another aspect of the invention, a method is provided for restoring the height of a vertebral body comprising the steps of: engaging a working channel cannula to the vertebral body to access the interior of the vertebral body; introducing the distraction component into the interior of the bone using an inserter extending through the working channel cannula to restore the height of the vertebral body; and injecting a fluent material through the same working channel adjacent the distraction component. In certain embodiments, the inserter is removed from the working channel cannula before the fluent material is injected.

In this embodiment, the distraction component may include a plurality of stacked wafers, and the step of introducing the distraction component may include extending a wafer introducer into the working channel cannula and operating the wafer introducer to introduce the plurality of stacked wafers into the interior space. Accordingly, the step of injecting a fluent material may include extending an injection cannula into the working channel cannula and directly adjacent the distraction component. As with the previous embodiment, the injecting step includes injecting the fluent material under pressure, preferably at a pressure less than a pressure at which extravasion occurs from the bone.

In yet another feature of the invention, a system is contemplated for restoring the height of a vertebral body, comprising: a working channel cannula configured to access the interior of the vertebral body; an inserter for inserting a distraction component through the working channel into the interior of the vertebral body; and an injection cannula configured to extend through the working channel cannula into the interior of the vertebral body, the injection cannula having a proximal end configured to connect to a source of a fluent material and a distal end defining at least one opening for discharge of the fluent material.

The injection cannula may include an orientation marker at a proximal portion thereof, the marker aligned with the at least one opening to provide a visual indication of the orientation of the opening within the interior of the vertebral body. Moreover, the injection cannula may include a plurality of openings at the distal end. In certain embodiments, the distraction component has a length along its insertion direction, and the plurality of openings span a distance along a distal portion of the injection cannula that is substantially equal to the length of the distraction component.

In other embodiments, the injection cannula includes only one opening at the distal tip thereof. This opening is preferably angled relative to the longitudinal axis of the cannula to direct the fluent material at the distraction component.

It is one object of the present invention to provide methods and systems for introducing fluent material into a distraction site, preferably within a bone, like a vertebral body. Another object is achieved by features of the invention that ensure that the fluent material at least partially surround the distraction component. Another object is to inject the fluent material so that it interdigitates or combines with the surrounding cancellous portion of the bone. These and other objects and benefits can be discerned from the following written description and accompanying figures.

DESCRIPTION OF THE PREFERRED EMBODIMENTS

Figure 1:
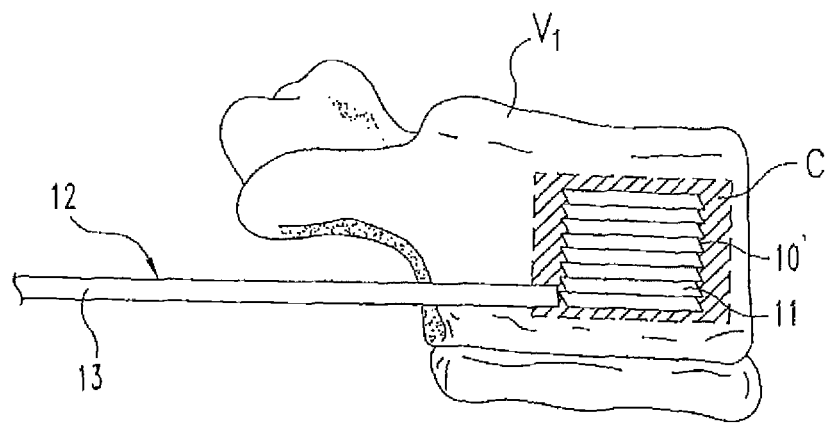
FIG. 1 is a side view of components of a tissue distraction system in accordance with the invention disclosed in U.S. Pat. No. 6,595,998.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates an adjunct to the wafer insertion system described in the '998 Patent discussed above. However, it should be understood that the devices and methods disclosed herein can be used with other percutaneously introduced distraction systems or tissue filler delivery systems. The following description of the invention focuses on a use in conjunction with the restoration of a vertebral body following a compression fracture. It should be further understood that the devices and methods disclosed herein may also be used in connection with other procedures in which tissue surfaces are distracted.

Figure 3:
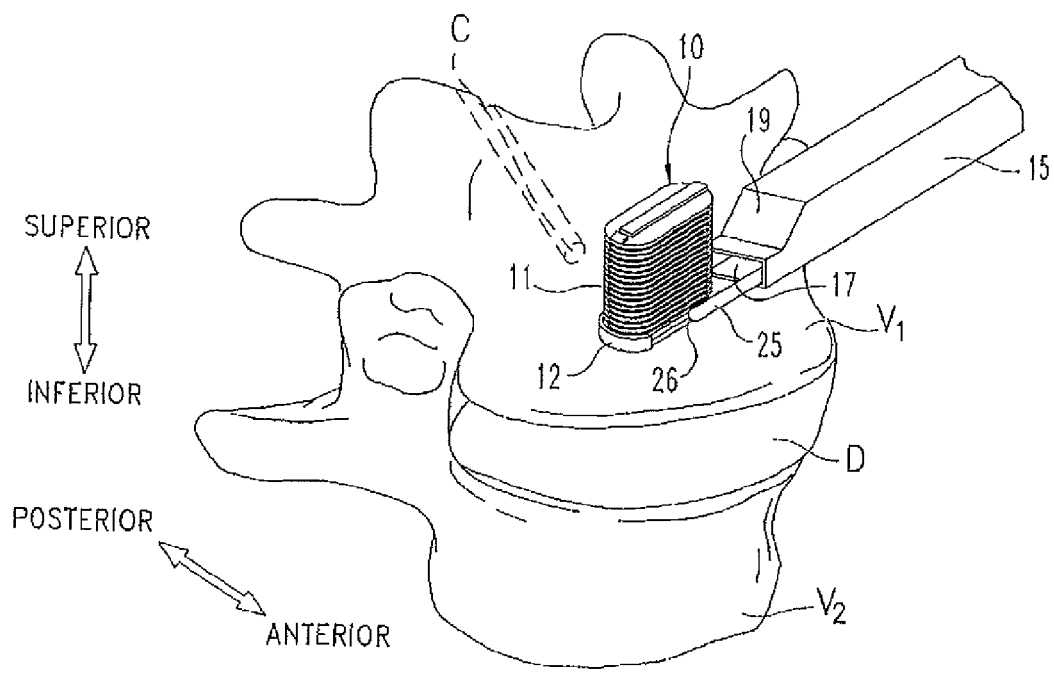
FIG. 3 is a perspective view of the distal end of a device in accordance with one embodiment of the present invention for injecting a fluent material into the vertebral body supported by a wafer stack.

Referring now to FIG. 3, a perspective view of a vertebral body V1 is depicted in which access to the cancellous bone C has been provided through conventional means. The superior and inferior bony surfaces of the body V1 have been distracted and are supported by a stack 10, which may be formed by a plurality of wafers 11 introduced using the wafer inserter 12 in a manner described in U.S. Pat. No. 6,595,998, the disclosure of which has been incorporated herein by reference. The wafer inserter 12 is preferably positioned anterolaterally within the lateral cortical bone of the vertebral body $V_1$, as shown in FIGS. 1, 3. More specifically, the wafer inserter is extended through a working channel cannula 15 of the present invention, exiting at a distal opening 17 through which the wafers are pushed into the cancellous bone C.

Figure 4:
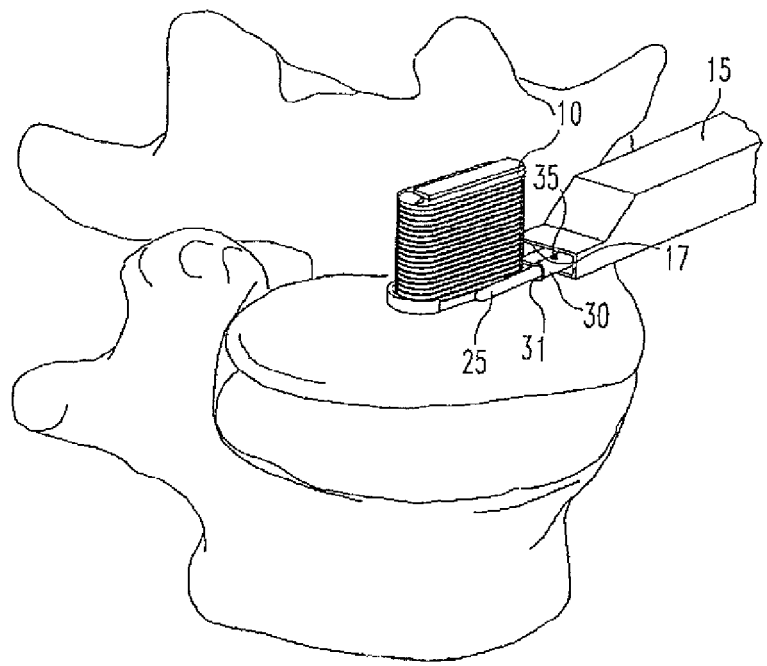
FIG. 4 is a perspective view of the device shown in FIG. 3, including an injector cannula.

In one embodiment, the distal end of the cannula 15 may include a beveled surface 19 that engages the cortical bone and helps stabilize the cannula 15 while the wafers 11 are inserted. In addition, the beveled surface 19 helps position the distal opening 17 at an appropriate location within the vertebral body $V_1$ for optimum placement of the wafer stack 10. In a preferred method of the invention, the working channel cannula is driven into an access port cut into the bone. The cannula 15 is driven into the cortical bone until the opening 17 is positioned within the interior of the bone (i.e., the cancellous bone). The working channel cannula can be driven into position by striking the proximal end of the cannula directly with a mallet. Optionally, a tamp can be fed through the cannula 15 and the mallet can strike the handle of the tamp to push the tamp into the bone and then to embed the cannula within the access port in the bone. Once the working channel cannula is in its operative position, as shown in FIGS. 3-4, the tamp is removed. A second tamp having depth markings may be introduced through the working channel cannula to prepare the interior of the bone to receive the distraction component or wafers. This second tamp may also be used to determine the depth within the bone to select an appropriately sized wafer for insertion.

Figure 6:
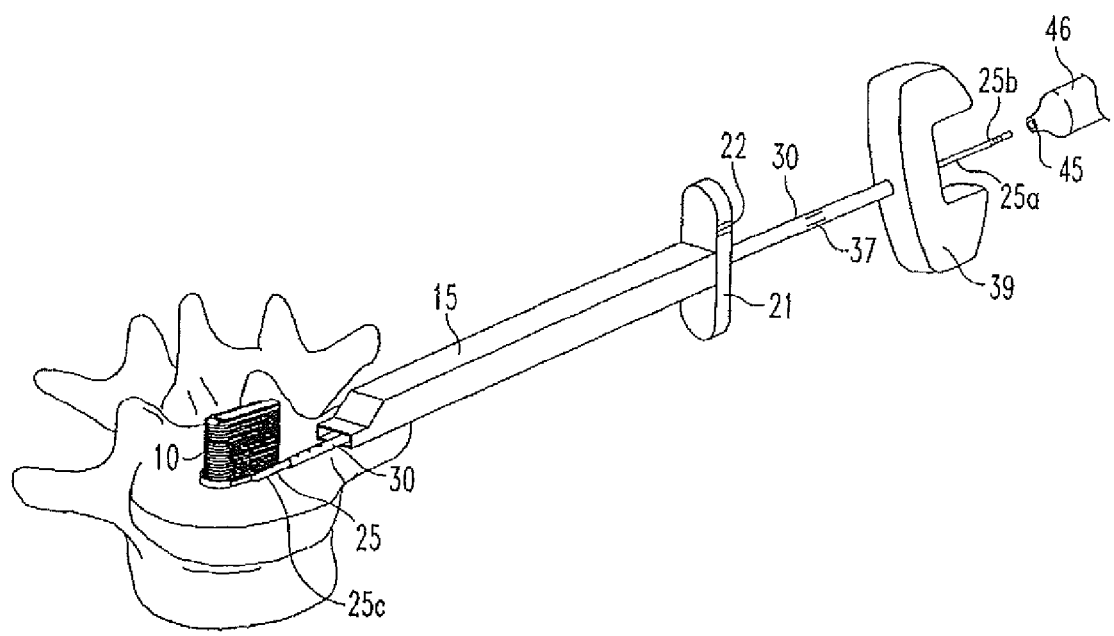
FIG. 6 is a perspective view of the complete device for injecting a fluent material shown in FIG. 3.

As shown in FIG. 6, the working channel cannula 15 may include a handle 21 at its proximal end that facilitates placement and manipulation of the cannula. The handle 21 may be provided with markings 22 that serve to identify the orientation of the cannula upon insertion. More particularly, the markings 22 indicate the position of the distal opening 17, which is preferably immediately adjacent the vertebral endplate at the disc D.

Figure 5:
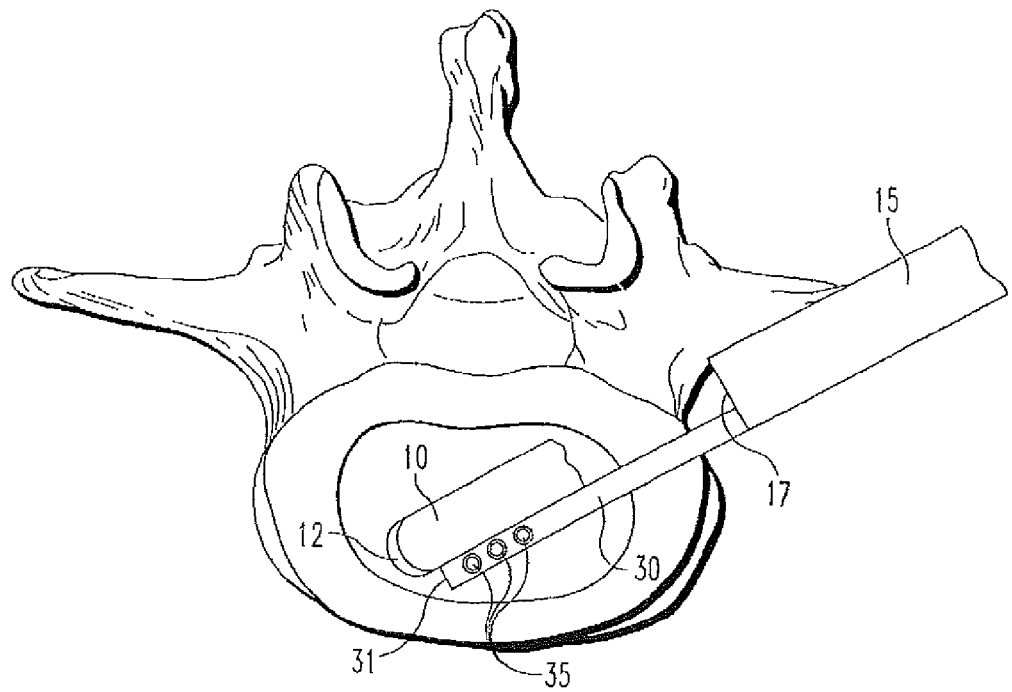
FIG. 5 is an inferior view of a vertebral body showing the position of the injector cannula within the body.

In accordance with the preferred embodiment of the present invention, the width of the distal opening 17 of the cannula, as well as the working width of the channel within the cannula, is greater than the width of the wafer stack 10. Moreover, the width of the opening 17 is greater than the width of the track 13 of the wafer inserter 12. In certain embodiments, the opening 17 may be made even wider to provide a passageway for a guide wire 25 so that the blunt end 26 of the guide wire may travel immediately adjacent the stack 10, as shown in FIG. 3, and for the injection cannula 30, as shown in FIGS. 4-6. Once at least one wafer has been inserted into the vertebral body $V_1$ to form the stack 10, the guide wire 25 may be introduced into the cancellous bone adjacent the stack without removing the cannula. In the preferred method of the invention, the guide wire and ultimately the injection cannula are extended through the working channel cannula 15 after the wafer inserter 12 has been removed.

Preferably, the proximal end 25a of the guide wire projects beyond the proximal end of the cannula, as illustrated in FIG. 6. The proximal end of the guide wire may include depth markings 25b that are calibrated to the distal end of the stack within the cancellous bone. It can be appreciated that the depth markings 25b provide a visual gauge relative to the working channel cannula 15 or more particularly relative to the handle 21. The location of the markings 25b on the guide wire depends upon whether the position of the markings is gauged with the working channel cannula 15 engaged with the cortical bone, as shown in FIG. 3, or with the cannula retracted as depicted in FIG. 5. The markings 25b can extend along the proximal length of the guide wire to serve as an indicator for the position of the injection cannula 30 relative to the wafer stack 10. The depth markings can be used to orient the tip of the guide wire 25 at predetermined positions relative to the wafer stack 10. For instance, in one specific embodiment of the method, the guide wire is inserted until the tip is positioned at the midpoint of the stack, while in another embodiment the guide wire tip reaches the farthest end of the stack.

Once the guide wire 25 has been positioned adjacent the wafer stack, the injection cannula 30 may be deployed concentrically over the wire, as shown in FIGS. 4-6. It can be appreciated that the opening 17 (as well as the cannula channel) has a height sufficient to accommodate not only the guide wire 25, but also the injection cannula 30 threaded over the guide wire. With this aspect of the invention, the height of the working channel cannula opening 17 may be greater than the thickness of one of the wafers 11 being pushed through the cannula 15.

The injection cannula provides an avenue for percutaneous introduction of fluent material into the vertebral body $V_1$, as well as into the cancellous bone C, without the need for more invasive surgery. The injection cannula 30 of the present invention thus provides one advantage of being capable of introduction through the same working channel cannula 15 used to introduce the distraction components into the vertebral body $V_1$. The working channel may be sized to accommodate introduction of the injection cannula even when the wafer insertion components are situated within the working channel.

Figure 7:
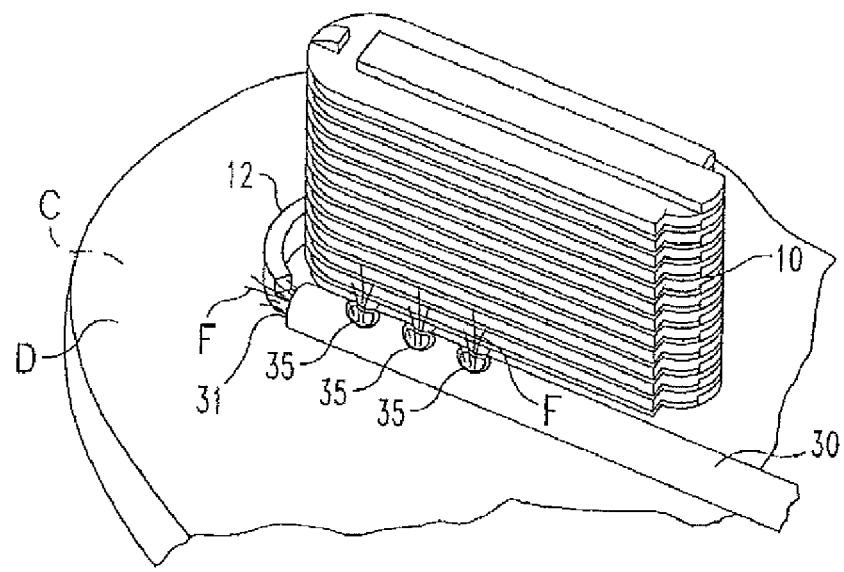
FIG. 7 is an enlarged rear perspective view of the working end of the device depicted in FIGS. 3-6 with the injection cannula adjacent a wafer stack supporting the distracted tissue surfaces.
Figure 8:
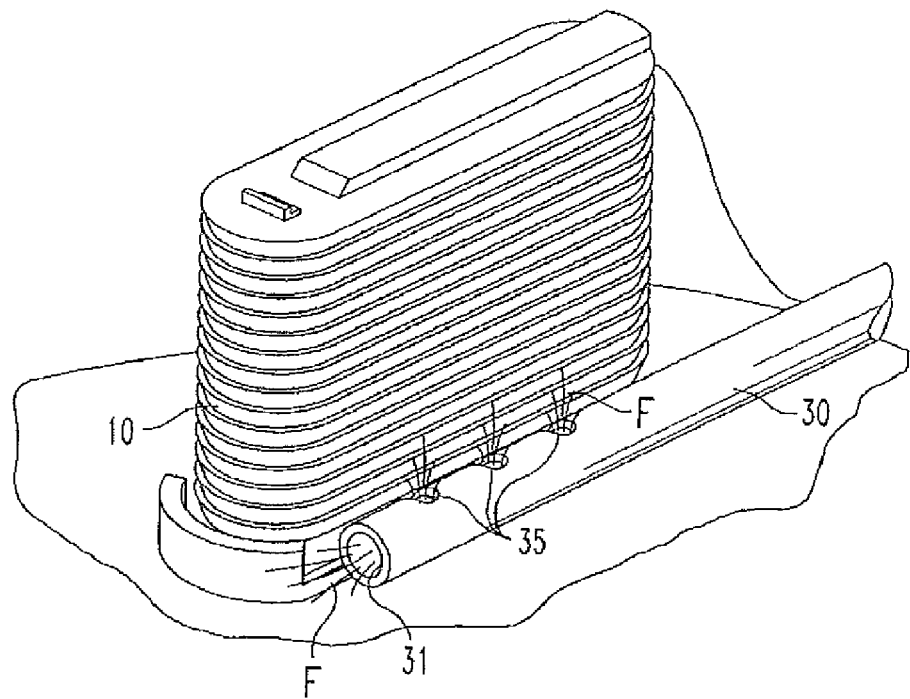
FIG. 8 is an enlarged front perspective view of the working end of the device shown in FIG. 7 in accordance with one embodiment of the invention.

As shown in FIGS. 4-5, the injection cannula 30 includes a distal opening 31 so that the cannula may be threaded over the guide wire. In one embodiment, the injection cannula defines several discharge openings 35 that communicate with the interior channel of the cannula. In one feature of the invention, the openings 35 are all oriented in the same direction (superior facing in FIGS. 4-6). More particularly, the openings 35 are arranged and aligned so that fluid dispensed from the injection cannula 30 will flow past the side of the stack 10. The flow F of fluent material may be directed to the front and the sides of the stack 10, as best seen in FIG. 7, so that the fluent material will eventually surround stack 10. In accordance with the present invention, the openings in the cannula are configured so that the fluent material can be injected directly into the interior of the bone and directly adjacent the length of the wafer stack.

The number and extent of the openings can be set by the nature of the fluent material being injected into the cancellous bone C adjacent the stack 10. In the illustrated embodiment, three openings 35 are provided and are evenly spaced along the distal portion of the injection cannula 30. In this embodiment, the distal opening 31 is situated near the end of the stack and the most proximal of the openings 35 is situated at about one-third of the length of the stack. These openings in this illustrated embodiment are well suited for impregnating the cancellous bone C adjacent the stack with bone cement in an effort to reduce the pain associated with the fracture. In addition, the arrangement of the openings allows introduction of bone cement around at least a portion of the stack 10 to help stabilize the stack. Of course, additional openings can be provided proximal to the last opening shown in FIG. 7 so that the openings span the entire length of the stack 10. In addition, the end opening 31 can be eliminated in favor of introducing the fluent material only at the sides of the stack.

The size of the openings may be calibrated to the type of fluent material, and more particularly to the viscosity of the material, and to the pressure at which the material is injected. It is preferable that the injection pressure be as low as possible while still achieving complete coverage of the stack 10 by the injected material. If the injection pressure is too great, the risk of extravasation increases. In some cases, the pressure and material viscosity can be sufficient to impregnate and interdigitate with the cancellous bone surrounding the stack.

Referring to FIG. 6, it can be seen that that injection cannula 30 extends beyond the length of the working channel cannula 15, but is preferably stopped short of the distal end 25c of the guide wire 25. The injection cannula includes a handle 39 for supporting the cannula while the fluent material is injected. The injection cannula 30 preferably includes orientation markings 37 that are aligned with the direction of the openings 35 to allow the surgeon to determine that the openings are facing the proper direction relative to the stack and the distracted tissue. The orientation markings may also be used to determine the depth of insertion of the cannula and ensure that the distal opening 31 and/or openings 35 are properly positioned relative to the stack.

Once the injection cannula is positioned within the cancellous bone C, the guide wire 25 is removed. This frees the channel of the injection cannula 30 for the passage of fluent material. The handle 39 of the injection cannula 30 may be configured to provide an anchor for attachment of a source for the fluent material. In the preferred embodiment, that source is a hypodermic syringe 46 as shown in FIG. 6. (Of course, the guide wire will not be in the position shown in FIG. 6 when the syringe is engaged to the handle 39). In accordance with the present invention, hypodermic syringes are pre-loaded with the fluent material to be introduced. More than one syringe may be required depending upon the volume of the material to be introduced. Moreover, the syringes may contain different fluent material, for instance where a catalyst is required to activate a particular material. The handle 39 of the injection cannula 30 may be configured to allow removal of one syringe and replacement with another pre-loaded syringe. Thus, the handle 39 may define a recess concentric with the opening for the injection cannula and configured for a press-fit engagement with the tip 45 of the syringe 46.

In the illustrated embodiment, the syringe is operated manually and the injection pressure is controlled by the amount of pressure applied to the syringe plunger. Nominally, the amount of injection pressure that can be generated by a syringe is less than the pressure at which extravasation becomes a problem. In an alternative, the source of fluent material may be a powered device, such as a pump, although care must be taken to limit the injection pressure, as discussed above.

In one embodiment of the invention, the fluent material is a hardenable material, such as PMMA (polymethylmethacrylate). The PMMA impregnates or integrates with the cancellous bone adjacent the distraction component or stack 10 to help stabilize the fractured body. It is believed that pain associated with certain fractures, such as a vertebral compression fracture, arises due to micro-motion of the fractured bone. Adding a structural support, such as the wafer stack 10, restores the patency and height of the fractured bone, while the addition of the fluent material helps stabilize the bone by reducing this micro-motion. One acceptable PMMA is SIMPLEX™ by Stryker Corp. Other hardenable or "structural" materials, such as HAP (hydroxyapatite), may be injected through the cannula 30 to help stabilize the cancellous bone and/or stabilize the distraction component. These structural materials may or may not augment the structural support or load bearing capabilities of the stack 10.

In other embodiments of the invention, the injected fluent material is a non-load bearing or non-structural material (i.e., the material does not harden into a support column of material). In some cases, the non-structural fluent material will help stabilize the cancellous bone adjacent the stack. In other cases, the fluent material does not provide any stabilizing effect, but is instead provided as a vehicle for other beneficial or therapeutic features. In certain embodiments, the fluent material may be osteo-inductive, such as BMP (bone morphogenic protein), osteo-conductive, such as HAP, or pharmaceutical materials. In one specific embodiment, the fluent material injected through the openings 31 and 35 is a bone filler material, such as OSTEOFIL®, marketed by Medtronic Sofamor, or GRAFTON®, produced by Osteotech, that integrates with the cancellous bone surrounding the stack 10.

In a modification of the method of the present invention, the working channel cannula may be at least partially withdrawn once the guide wire 25 is in position. Thus, as shown in FIG. 5, the cannula 15 is dislodged from the bone opening and retracted slightly. Retracting the working channel cannula 15 provides greater clearance for manipulation of the injection cannula 30.

In a specific embodiment, the guide wire 25 is a standard 1.6 mm diameter wire. Thus, the injection cannula 30 has an inner diameter of at least 1.65 mm, and preferably about 1.8-2.0 mm with an outer diameter of about 3.0-3.5 mm. The size of the opening 17 of the working channel cannula 15 is dictated by the size of the wafers that form the stack 10, which may range from 2 to 12 mm in width and 0.2-6.0 mm in thickness, for example. The wafer size determines the dimensions of the track 13 of the wafer inserter 12, and the cannula 15 must be sized to receive that track therein. Thus, at a minimum, the cannula opening 17 may have a width of about 5 to 15 mm and a height of 2 to 8 mm. In some embodiments, the cannula is sized to simultaneously accommodate the wafer inserter and the injection cannula, so the largest overall width of the opening 17 may range from about 10 mm for the smallest wafers to about 20 mm for the largest wafers.

Figure 9:
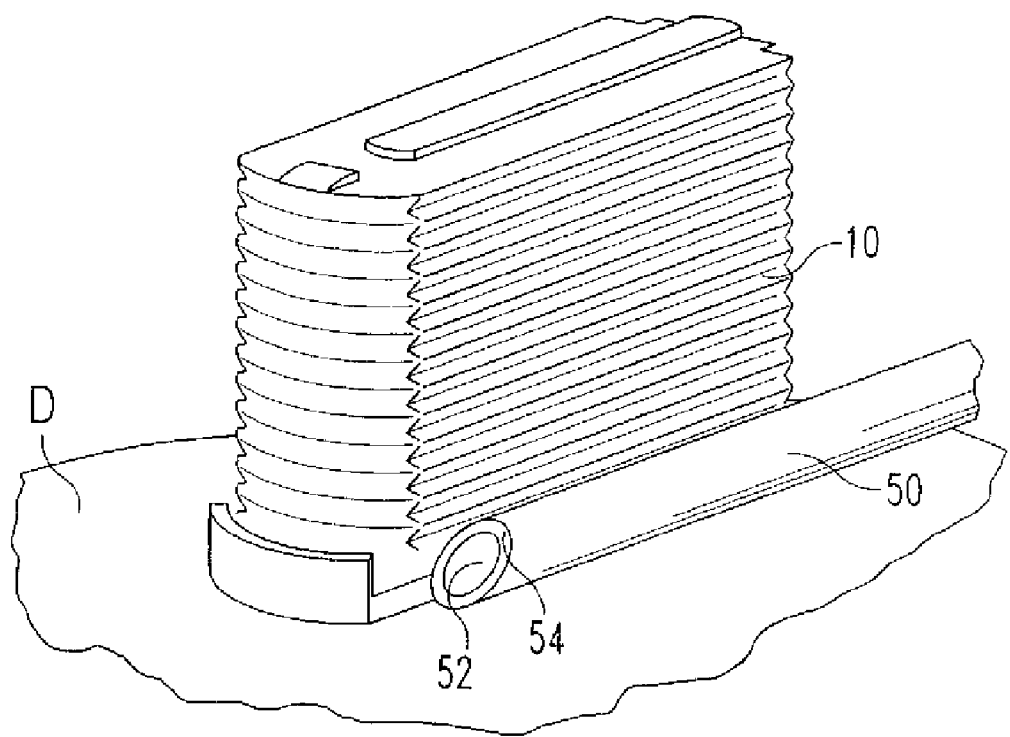
FIG. 9 is an enlarged front perspective view of the working end of an alternative embodiment of a device for injecting fluent material.

In a further embodiment of the invention, the injection cannula may be modified to the cannula 50 illustrated in FIG. 9. In particular, the injection cannula 50 does not include the side openings, such as the openings 35 of the cannula 30 depicted in FIG. 7. Instead, the cannula 50 relies upon providing an angled edge 54 for a discharge opening 52 at the distal end of the cannula. In this instance, the fluid flow will be directed upward and distally. With this embodiment, the injection cannula is preferably slowly withdrawn as the fluent material is discharged through the opening 52. With this approach, the amount of fluid at any particular station along the length of the stack 10 can be controlled. For instance, the opening 52 may be maintained at the end of the stack for a set length of time before the cannula 50 is retracted to provide more fluent material at the end 12 of the stack.

In yet another variation of the invention, the working channel cannula 15 and the injection cannula 30 is used for bifurcated injection. In other words, the injection cannula may be positioned adjacent one side and then adjacent the opposite side of the stack 10 to inject the fluent material on both sides of the height restoring distraction component. The working channel cannula 15 may have a width sufficient to provide clearance for the wafers 11 and an injection cannula 30 on both sides of the wafers. Alternatively, the two cannulae may be manipulated to position the injection cannula adjacent one side or the other of the stack 10. This manipulation is best accomplished with the working channel cannula offset from the vertebral body $V_1$, as shown in FIG. 5.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

Figure 2:
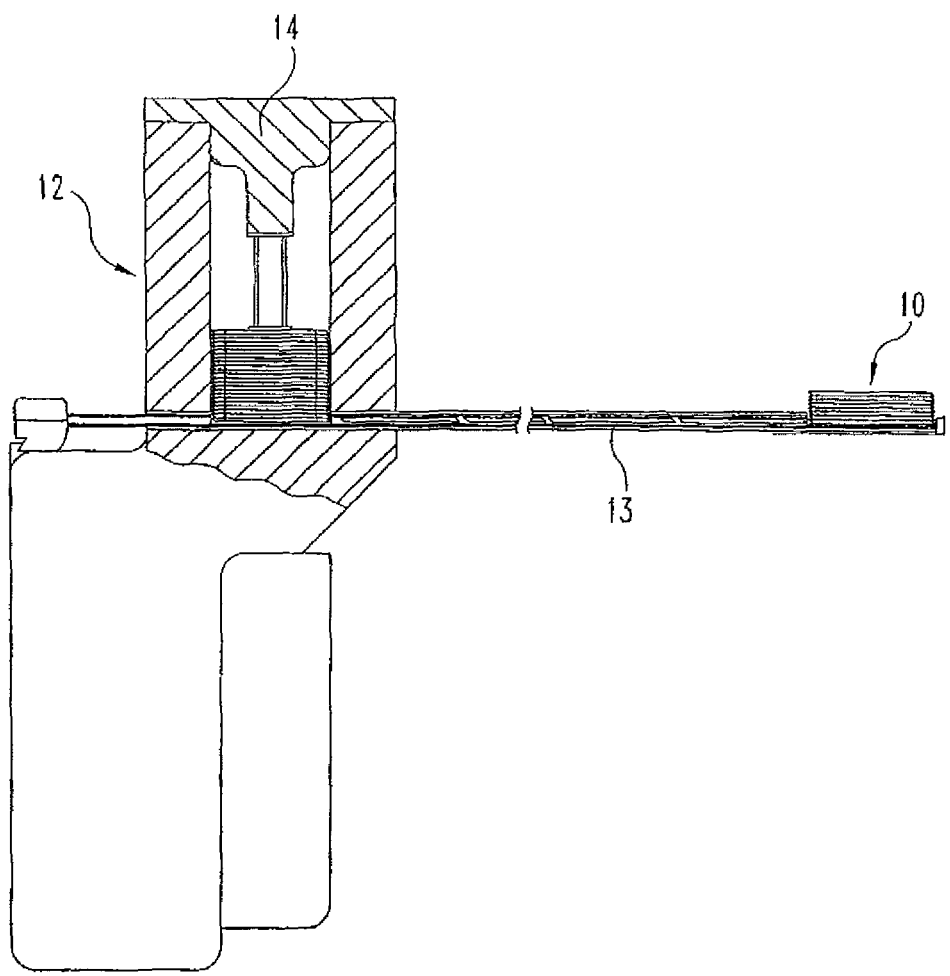
FIG. 2 is a side partial cross-section view of a wafer inserter device disclosed in the '998 Patent.

For example, while the embodiments described above contemplate injecting the fluent material after the stack 10 has been constructed and the space distracted, the injection step can occur at any point in the distraction process. Thus, the injection tube can be maintained within the working channel cannula 15 as the wafers forming the stack are sequentially introduced. Structural (load-bearing or hardenable) or nonstructural material can be introduced at any time. For instance, the fluent material can be a binder composition that binds the wafers upon curing, so an amount of the composition may be introduced as each new wafer is inserted into the stack. Of course, with this approach, the injection cannula 30 and handle 39 may require modification so as to avoid interference with the wafer inserter 13 (FIG. 2), such as by lengthening the injection cannula 30 to move clear of the inserter. The body of the wafer inserter can be modified to help support the cantilevered injection cannula.

As a further alternative, the positioning of the discharge openings 35 can be modified from that shown in FIGS. 5-7. For instance, some of the openings can be aligned to direct the fluent material directly into or directly away from the stack 10. Similarly, the openings can be configured to discharge the fluent material at an angle along the side of the stack.

What is claimed is:

1. A system for restoring the height of a vertebral body, comprising:
 a working channel cannula having a proximal end and a distal end, said distal end being configured to access the interior of the vertebral body, said working channel cannula having a central axis and an interior channel having a transverse extent;
 an elongate distraction component having a distal end and a proximal end and two opposing sides therebetween;
 an inserter for inserting said elongate distraction component through said working channel into the interior of the vertebral body; and
 an elongate injection cannula configured to extend through said working channel cannula into the interior of the vertebral body, said injection cannula having a proximal end configured to connect to a source of a fluent material and a distal end defining at least one opening for discharge of the fluent material, said injection cannula being of size and configuration to be disposed in said interior channel with the distal end of said injection cannula lying adjacent to one of the sides of said elongate component.

2. The system of claim 1, wherein said injection cannula includes an orientation marker at a proximal portion thereof, said marker aligned with said at least one opening to provide a visual indication of the orientation of the opening within the interior of the vertebral body.

3. The system of claim 1, wherein said injection cannula includes a plurality of openings at said distal end.

4. The system of claim 3, wherein said plurality of openings span a distance along a distal portion of said injection cannula that is substantially equal to the length of the distraction component.

5. The system of claim 1, further comprising a syringe operating as the source of the fluent material.

6. The system of claim 1, wherein said injection cannula includes only one opening at the distal tip thereof, said opening being angled relative to the longitudinal axis of the injection cannula.

7. The system of claim 1, wherein:
 said inserter has an inserter width less than said channel transverse extent; and
 the elongate distraction component has a length along its insertion direction and a transverse dimension transverse to said length, said transverse dimension being less than said inserter width.

8. The system of claim 7, wherein said injection cannula is configured to extend into the interior of the vertebral body adjacent to and generally parallel to said length of the elongate distraction component when said injection cannula extends through said working channel cannula with said distal end of said injection cannula projecting distally beyond the distal end of the working channel cannula.

9. The system of claim 1, wherein the outer dimension of said injection cannula is less than the transverse extent of said interior channel and is configured to be disposed in said interior channel with the longitudinal axis of said injection cannula offset from the central axis of said working channel cannula.

10. A system for restoring the height of a vertebral body, comprising:
 a working channel cannula having a proximal end and a distal end , said distal end being configured to access the interior of the vertebral body, said working channel cannula having a central axis and an interior channel having a transverse extent;

an elongate distraction component having a length between a distal end and a proximal end and two opposing sides therebetween;

an inserter for inserting said elongate distraction component through said working channel into the interior of the vertebral body;

an elongate injection cannula configured to extend through said working channel cannula into the interior of the vertebral body, said injection cannula having a proximal end configured to connect to a source of a fluent material and a distal end defining at least one opening for discharge of the fluent material, the outer dimension of said injection cannula being less than the transverse extent of said interior channel and configured to be disposed within said interior channel and manipulable rotationally and translationally therewithin with the distal end of said injection cannula of extent to lie adjacent to one of the sides of said elongate distraction component; and a fluent material having a viscosity for injection into said injection cannula and flow through said at least one opening under pressure.

11. The apparatus of claim 10, wherein said at least one opening is disposed at the distal tip of said injection cannula such the fluent material flows longitudinally from said injection cannula.

12. The apparatus of claim 10, wherein said at least one opening is disposed radially through said cannula such that fluent material flows radially from said injection cannula.

13. The apparatus of claim 12, wherein there are a plurality of such radially disposed openings spaced along said injection cannula, said openings being arranged in a common orientation relative to the longitudinal axis of said injection cannula.

14. The apparatus of claim 10, wherein the fluent material is a hardenable material.

15. The apparatus of claim 14, wherein the hardenable material is a bone cement.

16. The apparatus of claim 10, wherein the fluent material is selected from the group containing bone morphogenic protein, osteo-inductive compositions, osteo-conductive compositions and pharmaceutical compositions.

17. The apparatus of claim 10, wherein said injection cannula includes an orientation marker adjacent the proximal end of said injection cannula and aligned with said at least one opening.

18. The apparatus of claim 10, wherein said injection cannula includes depth markings adjacent the proximal end of said injection cannula for providing an indication of the depth of insertion of the distal end of said injection cannula into cancellous bone.

19. The apparatus of claim 10, wherein said injection cannula further includes a handle disposed adjacent the proximal end thereof for supporting said injection cannula during injection of said fluent material into said injection cannula.

20. The apparatus of claim 19, wherein said handle is configured for attachment to said source of fluent material.

21. The apparatus of claim 20, wherein said source of fluent material comprises a syringe.

22. The apparatus of claim 10, wherein said working channel cannula further includes a handle disposed adjacent the proximal end thereof to facilitate placement of said working channel cannula into said vertebral body.

23. The apparatus of claim 10, wherein said injection cannula is configured to be disposed in said interior channel with the longitudinal axis of said injection cannula offset from the central axis of said working channel cannula.

24. The system of claim 10, wherein said injection cannula has an extent such that said distal end of said injection cannula projects distally beyond the distal end of the working channel cannula.

25. The apparatus of claim 10, wherein the fluent material is a non-structural fluid.

* * * * *